(12) United States Patent
Heidelbaugh et al.

(10) Patent No.: US 7,868,020 B2
(45) Date of Patent: Jan. 11, 2011

(54) QUINOLYNYLMETHYLIMIDIZOLES AS THERAPEUTIC AGENTS

(75) Inventors: Todd M. Heidelbaugh, Fountain Valley, CA (US); Phong X. Nguyen, Placentia, CA (US); Ken Chow, Newport Coast, CA (US); Michael E. Garst, Newport Beach, CA (US)

(73) Assignee: Allergan, Inc., Irvine, CA (US)

( * ) Notice: Subject to any disclaimer, the term of this patent is extended or adjusted under 35 U.S.C. 154(b) by 36 days.

(21) Appl. No.: 12/522,887

(22) PCT Filed: Jan. 4, 2008

(86) PCT No.: PCT/US2008/050156
§ 371 (c)(1),
(2), (4) Date: Jul. 10, 2009

(87) PCT Pub. No.: WO2008/088936
PCT Pub. Date: Jul. 24, 2008

(65) Prior Publication Data
US 2010/0113516 A1  May 6, 2010

Related U.S. Application Data

(60) Provisional application No. 60/884,718, filed on Jan. 12, 2007, provisional application No. 60/917,828, filed on May 14, 2007.

(51) Int. Cl.
*A61K 31/47* (2006.01)
*C07D 215/12* (2006.01)

(52) U.S. Cl. .................. 514/311; 546/152

(58) Field of Classification Search .............. 514/311; 546/152
See application file for complete search history.

(56) References Cited

U.S. PATENT DOCUMENTS

| | | |
|---|---|---|
| 4,814,343 A | 3/1989 | Cossement |
| 5,151,526 A | 9/1992 | Hsu et al. |
| 6,329,369 B1 | 12/2001 | Chow et al. |
| 6,465,486 B1 | 10/2002 | Baxter |
| 6,841,684 B2 | 1/2005 | Chow et al. |
| 2002/0019390 A1 | 2/2002 | Wong et al. |
| 2003/0023098 A1 | 1/2003 | Chow et al. |
| 2006/0069144 A1 | 3/2006 | Heidelbaugh |

FOREIGN PATENT DOCUMENTS

| | | |
|---|---|---|
| EP | 0 024 829 | 8/1980 |
| EP | 1 413 576 | 12/1998 |
| WO | WO 98/46572 | 10/1998 |
| WO | WO 99/28300 | 6/1999 |
| WO | WO 01/00586 | 1/2001 |
| WO | WO 02/076950 | 10/2002 |
| WO | WO 2006/036497 | 4/2006 |
| WO | WO 2006/036507 | 4/2006 |

OTHER PUBLICATIONS

Prezeslawski R., et al.; "Synthesis and Alpha2-Adrenergic Activity of Quinoline and Quinoxaline Analogues of Medetomidine"; Proceedings of the Erdec Scientific Conference on Defense Research; Nov. 1994; pp. 121-127; XP008091151.*
Seoung-Soo Hong et al.; "A Structure-Activity Relationship Study of Benzylic Modifications of 441 -(I -Naphthyl)ethyl]-1H-imidazoleos n al- and az-Adrenergic Receptors"; J. Med. Chem. 1994,37, 2328-2333.
Shilpa G. Lalchandani, et al; "Medetomidine analogs as selective agonists for the human a2-adrenoceptors"; Biochemical Pharmacology 67 (2004) 87-96.
D.D Miller, et al.; "Synthesis and biological Activity of a Series of Comformationally Restricted Analogs of 4-Substituted Imidazoles as $a_2$-Adrenergic Agonists"; Proceedings of the Erdec Scientific Conference on Defense Research; Nov. 1994; pp. 113-119.
Yoshiya Amemiya et al.; "Medetomidine Analogs as $a_2$-Adrenergic Agonists"; Egypt J. Pharm. Sci. 35, No. 1-6, pp. 403-410; 1994.
Yoshiya Amemiya et al.; "Synthesis and a-AdrenergicActivvities of 2- and 4-Substituted Imidazoline and Imidazole Analogues of α and β-Naphthalene"; Egypt J. Pharm. Sci. 35, No. 1-6, pp. 91-112; 1994.
B. V. Venkataraman et at.; "Structure-Activity Studies of New Imidazolines on Adrenoceptors of Rat Aorta and Puman Platelets"; Naunyn-Schmiedeberg's Arch Pharma, 344:454-463; 1994.

* cited by examiner

*Primary Examiner*—Susannah Chung
*Assistant Examiner*—Janet L Coppins
(74) *Attorney, Agent, or Firm*—Doina G. Ene; John E. Wurst; Kevin J. Forrestal

(57) ABSTRACT

Disclosed herein is a compound of the formula (I):(I). Therapeutic methods, compositions and medicaments related thereto are also disclosed.

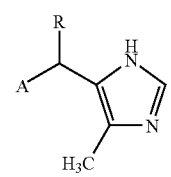

(1)

15 Claims, No Drawings

QUINOLYNYLMETHYLIMIDIZOLES AS THERAPEUTIC AGENTS

CROSS REFERENCE TO RELATED APPLICATIONS

This is a national stage application under 35 U.S.C. §371 of PCT patent application PCT/US08/050,156, filed on Jan. 4, 2008, which claims the benefit of U.S. Provisional Patent Application 60/884,718, filed Jan. 12, 2007 and U.S. Provisional Application Ser. No. 60/917,828, filed May 14, 2007, which is hereby incorporated by reference in its entirety.

DESCRIPTION OF THE INVENTION

Disclosed herein is a compound of the formula

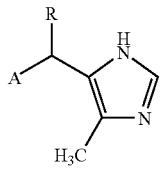

wherein R is H, $C_{1-4}$ alkyl, or $CF_3$;

A is tetrahydroquinolinyl having 0, 1, 2, or 3 stable substituents consisting of from 1 to 8 heavy atoms and any required hydrogen atoms, said heavy atoms being selected from C, N, O, S, F, Cl, Br, I, and any combination thereof.

Another embodiment is a method comprising administering a compound disclosed herein to a patient in need thereof for the treatment of glaucoma or ocular hypertension.

DEFINITIONS, EXPLANATIONS, AND EXAMPLES

Unless explicitly and unambiguously indicated otherwise, the definitions, explanations, and examples provided in this section shall be used to determine the meaning of a particular term or expression where there is any ambiguity arising from other parts of this document or from any disclosure incorporated by reference herein.

Hydrocarbyl is a moiety consisting of carbon and hydrogen, including, but not limited to:

1. alkyl, which is hydrocarbyl containing no double or triple carbon-carbon bonds; alkyl includes, but is not limited to:
   linear alkyl, cyclic alkyl, branched alkyl, and combinations thereof;
   $C_{1-4}$ alkyl, which refers to alkyl having 1, 2, 3, or 4 carbon atoms, including, but no limited to, methyl, ethyl, isopropyl, cyclopropyl, n-propyl, n-butyl and the like;
   $C_{1-6}$ alkyl, which refers to alkyl having 1, 2, 3, 4, 5, or 6 carbon atoms; including, but not limited to methyl, ethyl, propyl isomers, cyclopropyl, butyl isomers, cyclobutyl, pentyl isomers, cyclopentyl, hexyl isomers, cyclohexyl, and the like;
   combinations of these terms are possible, and their meanings should be obvious to those of ordinary skill in the art; for example $C_{1-6}$ linear alkyl would refer to $C_{1-6}$ alkyl which is also linear;

2. alkenyl, which is hydrocarbyl containing one or more carbon-carbon double bonds; alkenyl includes, but is not limited to:
   linear alkenyl, cyclic alkenyl, branched alkenyl, and combinations thereof;
   alkenyl having 1, 2, 3, or more carbon-carbon double bonds;

3. alkynyl, which is hydrocarbyl containing one or more carbon-carbon triple bonds; alkynyl includes, but is not limited to:
   linear alkynyl, cyclic alkynyl, branched alkynyl, and combinations thereof;
   alkynyl having 1, 2, 3, or more carbon-carbon double bonds;

4. aryl, provided that it contains no heteroatoms either in a ring or as a substituent;

5. combinations of any of the above;

6. $C_{1-4}$ hydrocarbyl, which refers to hydrocarbyl having 1, 2, 3, or 4 carbon atoms; and 7. $C_{1-6}$ hydrocarbyl, which refers to hydrocarbyl having 1, 2, 3, 4, 5, or 6 carbon atoms.

Alkoxy is O-alkyl, such as $OCH_3$, O-ethyl, O-isopropyl, and the like.

Mercaptoakyl is S-alkyl, such as SCH3, S-ethyl, S-isopropyl, and the like

Acyloxy is

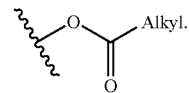

A compound, substituent, moiety, or any structural feature is stable if it is sufficiently stable for the compound to be isolated for at least 12 hours at room temperature under normal atmospheric conditions, or if it is sufficiently stable to be useful for at least one use disclosed herein.

A heavy atom is an atom which is not hydrogen.

A heteroatom is an atom which is not carbon or hydrogen.

A pharmaceutically acceptable salt is any salt that retains the activity of the parent compound and does not impart any additional deleterious or untoward effects on the subject to which it is administered and in the context in which it is administered compared to the parent compound. A pharmaceutically acceptable salt also refers to any salt which may form in vivo as a result of administration of an acid or another salt.

Pharmaceutically acceptable salts of acidic functional groups may be derived from organic or inorganic bases. The salt may comprise a mono or polyvalent ion. Of particular interest are the inorganic ions lithium, sodium, potassium, calcium, and magnesium. Organic salts may be made with amines, particularly ammonium salts such as mono-, di- and trialkyl amines or ethanol amines. Salts may also be formed with caffeine, tromethamine and similar molecules. Hydrochloric acid or some other pharmaceutically acceptable acid may form a salt with a compound that includes a basic group, such as an amine or a pyridine ring.

Unless otherwise indicated, reference to a compound should be construed broadly to include pharmaceutically acceptable salts, and tautomers of the depicted structure. For example, the structures herein are intended to include, but are not limited to, the tautomeric forms shown below.

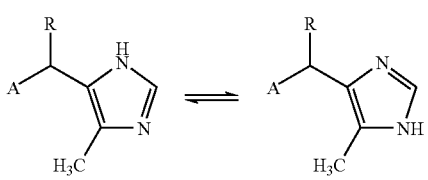

Unless stereochemistry is explicitly depicted, a structure is intended to include every possible stereoisomer, both pure or in any possible mixture.

For the purposes of this disclosure, "treat," "treating," or "treatment" refer to the use of a compound, composition, therapeutically active agent, or drug in the diagnosis, cure, mitigation, treatment, prevention of disease or other undesirable condition, or to affect the structure or any function of the body of man or other animals.

R is H, $C_{1-4}$ alkyl, or $CF_3$. Thus, the following compounds are contemplated.

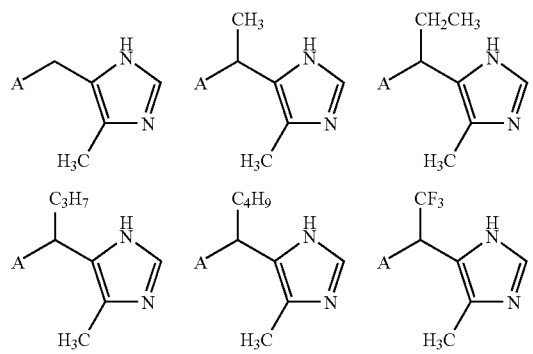

In one embodiment R is H.

A is tetrahydroquinolinyl having 0, 1, 2, or 3 stable substituents consisting of from 1 to 8 heavy atoms and any required hydrogen atoms, said heavy atoms being selected from C, N, O, S, F, Cl, Br, I, and any combination thereof.

Tetrahydroquinolinyl is one of the moieties depicted below:

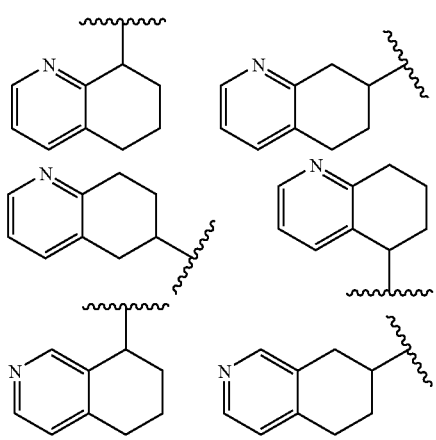

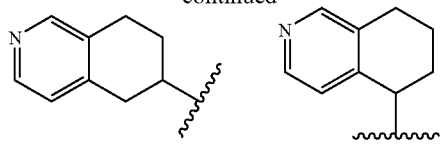

which may have substituents according to the parameters set forth herein.

Thus, for example, A may be any of the structures shown below or the like, wherein $R^1$, $R^2$, and $R^3$ are independently hydrogen or stable substituents consisting of from 1 to 8 heavy atoms and any required hydrogen atoms, said heavy atoms being selected from C, N, O, S, F, Cl, Br, I, and any combination thereof; and n is 0, 1, 2, or 3.

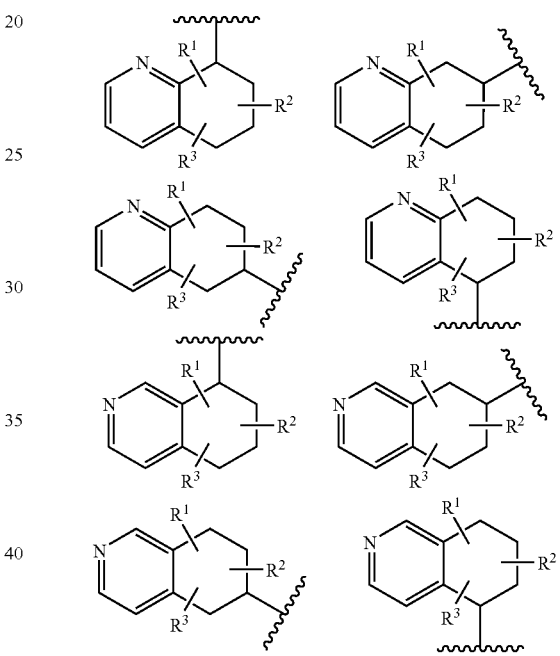

The position of $R^1$, $R^2$, and $R^3$ may be anywhere on the ring system, and are not limited to the particular ring where they are located in the structural depiction.

While not intending to be limiting, examples of stable substituents consisting of from 1 to 8 heavy atoms and any required hydrogen atoms include:

hydrocarbyl, including alkyl, such as methyl, ethyl, propyl isomers, butyl isomers, and the like; alkenyl, alkynyl, and phenyl;

alkoxy, mercaptoalkyl, acyloxy, amino, including $NH_2$, NH-alkyl, N(alkyl)$_2$, where the alkyl groups are the same or different;

halo, including F, Cl, Br, and I; and $CH_2CN$, CN; $NO_2$; OH.

If a substituent is a salt, for example of a carboxylic acid or an amine, the counterion of said salt, i.e. the ion that is not covalently bonded to the remainder of the molecule is not counted for the purposes of the number of heavy atoms in a substituent. Thus, for example, the salt —CO$_2^-$Na$^+$ is a stable substituent consisting of 3 heavy atoms, i.e. sodium is not counted. In another example, the salt —NH(Me)$_2^+$Cl$^-$ is a stable substituent consisting of 3 heavy atoms, i.e. chlorine is not counted.

In one embodiment, the substituents selected from are methyl, ethyl, propyl isomers, F, Cl, Br, I, OCH$_3$, NH$_2$, N(CH$_3$)$_2$, and combinations thereof.

In another embodiment substituents are selected from CH$_3$, ethyl, t-butyl, ethenyl, ethynyl, OCH$_3$, NHMe, NMe$_2$, Br, Cl, F, phenyl, and combinations thereof.

In another embodiment A is unsubstituted.

Another embodiment is a compound having the formula

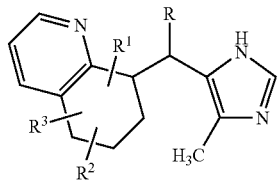

wherein R$^1$, R$^2$, and R$^3$ are independently hydrogen or stable substituents consisting of from 1 to 8 heavy atoms and any required hydrogen atoms, said heavy atoms being selected from C, N, O, S, F, Cl, Br, I, and any combination thereof; and n is 0, 1, 2, or 3.

Another embodiment is a compound having the formula

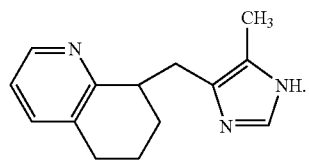

Another embodiment is a compound having the formula

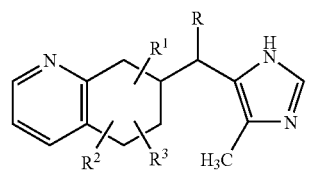

wherein R$^1$, R$^2$, and R$^3$ are independently hydrogen or stable substituents consisting of from 1 to 8 heavy atoms and any required hydrogen atoms, said heavy atoms being selected from C, N, O, S, F, Cl, Br, I, and any combination thereof; and n is 0, 1, 2, or 3.

Another embodiment is a compound having the formula

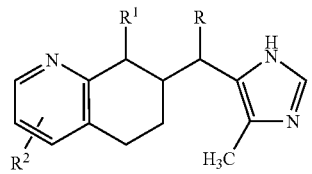

wherein R$^1$ and R$^2$ are independently hydrogen or stable substituents consisting of from 1 to 8 heavy atoms and any required hydrogen atoms, said heavy atoms being selected from C, N, O, S, F, Cl, Br, I, and any combination thereof; and n is 0, 1, 2, or 3.

Another embodiment is a compound having the formula

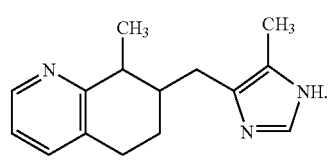

Another embodiment is a compound having the formula

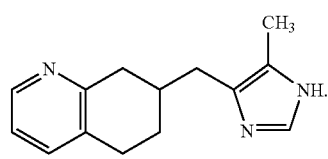

Biological Data

Receptor Selection and Amplification Technology (RSAT) Assay

The RSAT assay measures a receptor-mediated loss of contact inhibition that results in selective proliferation of receptor-containing cells in a mixed population of confluent cells. The increase in cell number is assessed with an appropriate transfected marker gene such as □-galactosidase, the activity of which can be easily measured in a 96-well format. Receptors that activate the G protein, Gq, elicit this response. Alpha2 receptors, which normally couple to Gi, activate the RSAT response when coexpressed with a hybrid Gq protein that has a Gi receptor recognition domain, called Gq/i5.

NIH-3T3 cells are plated at a density of 2×106 cells in 15 cm dishes and maintained in Dulbecco's modified Eagle's medium supplemented with 10% calf serum. One day later, cells are cotransfected by calcium phosphate precipitation with mammalian expression plasmids encoding p-SV-β-galactosidase (5-10 µg), receptor (1-2 µg) and G protein (1-2 µg). 40 µg salmon sperm DNA may also be included in the transfection mixture. Fresh media is added on the following day and 1-2 days later, cells are harvested and frozen in 50 assay aliquots. Cells are thawed and 100 µl added to 100 µl aliquots of various concentrations of drugs in triplicate in 96-well dishes. Incubations continue 72-96 hr at 37° C. After washing with phosphate-buffered saline, β-galactosidase enzyme activity is determined by adding 200 µl of the chromogenic substrate (consisting of 3.5 mM o-nitrophenyl-β-D-galactopyranoside and 0.5% nonidet P-40 in phosphate buffered saline), incubating overnight at 30° C. and measuring optical density at 420 nm. The absorbance is a measure of enzyme activity, which depends on cell number and reflects a receptor-mediated cell proliferation. The efficacy or intrinsic activity is calculated as a ratio of the maximal effect of the drug to the maximal effect of a standard full agonist for each receptor subtype. Brimonidine, also called UK14304, the chemical structure of which is shown below, is used as the standard agonist for the alpha$_{2A}$, alpha$_{2B}$ and alpha$_{2C}$ receptors. The EC$_{50}$ is the concentration at which the drug effect is half of its maximal effect.

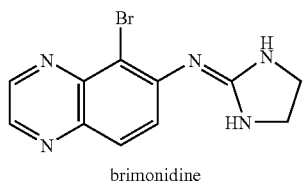
brimonidine

The results of the RSAT assay with several exemplary compounds of the invention are disclosed in Table 1 above together with the chemical formulas of these exemplary compounds. EC$_{50}$ values are nanomolar. NA stands for "not active" at concentrations less than 10 micromolar. IA stands for "intrinsic activity."

TABLE 1

| Structure | Alpha 1A EC50 (IA) | Alpha 2A EC50 (IA) | Alpha 2B EC50 (IA) | Alpha 2C EC50 (IA) |
|---|---|---|---|---|
| 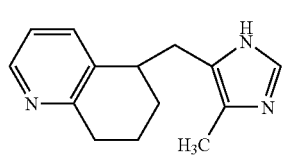 7 | 3340 (0.66) | NA | 57 (0.32) | 207 (0.63) |
| 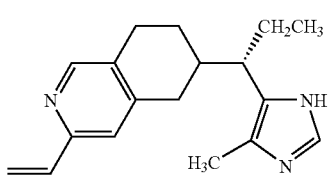 8 | 876 (0.66) | NA | 37 (0.7) | 366 (0.47) |

Compounds H5-H22 are hypothetical examples of compounds that are useful as disclosed herein.

H5

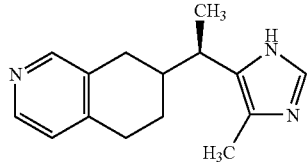 H6

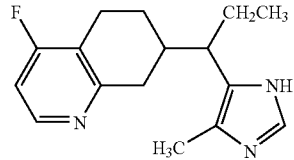 H7

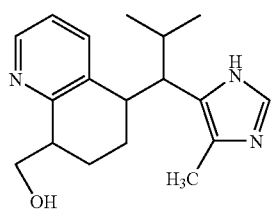 H8

-continued

H9

-continued
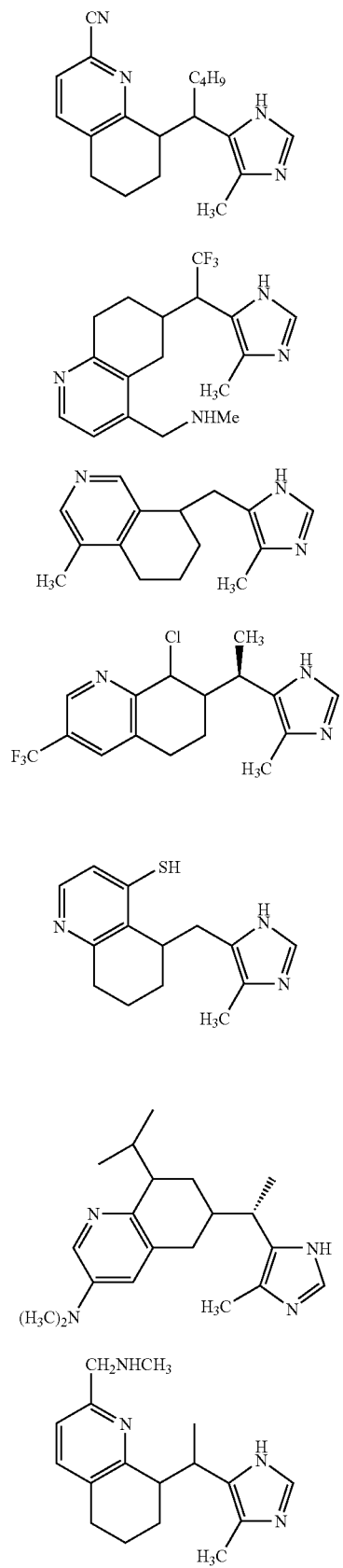
H10
H11
H12
H13
H14
H15
H16
-continued
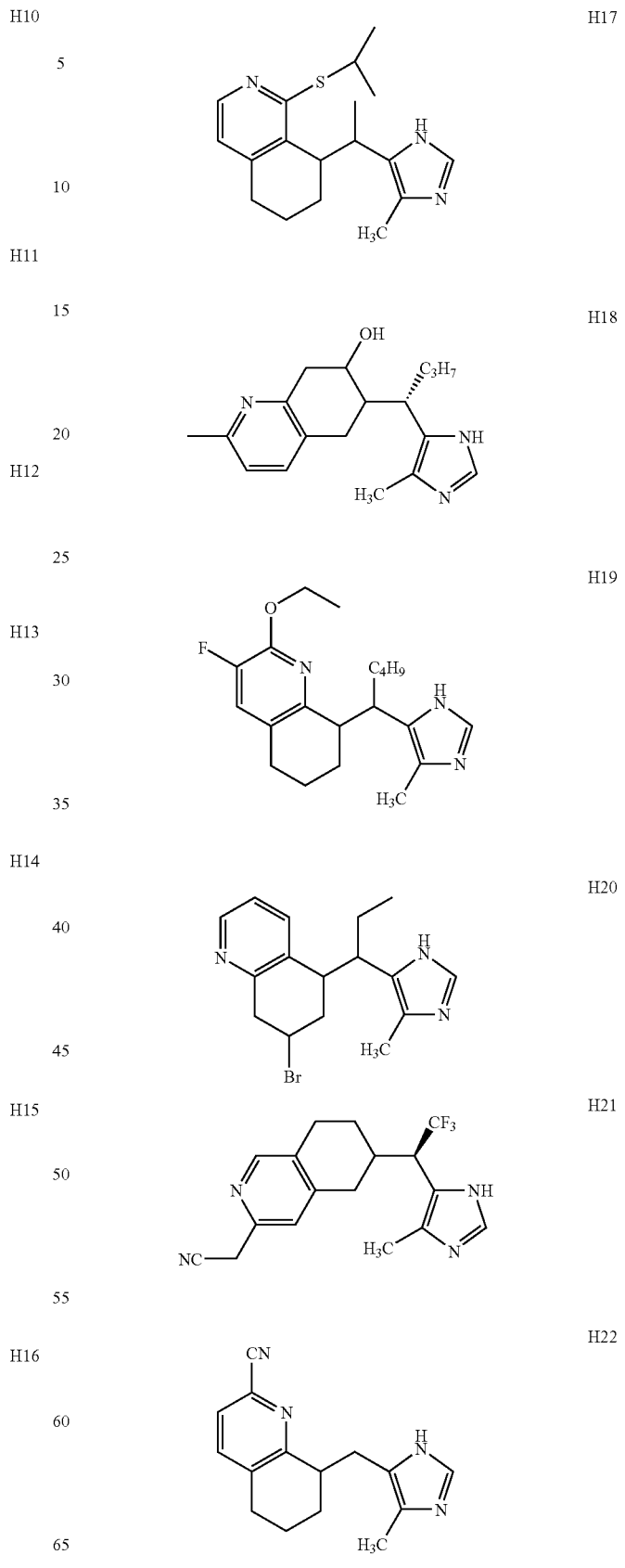
H17
H18
H19
H20
H21
H22

Synthetic Methods

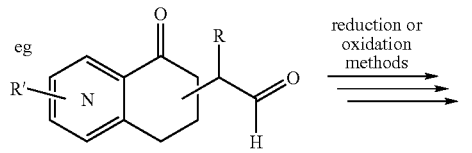

Scheme I

Starting material

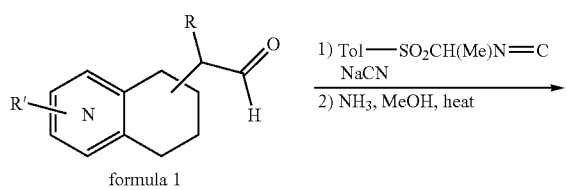

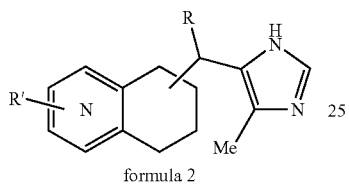

formula 2

In these schemes the structural depiction:

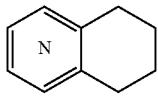

is intended to indicate that there is one nitrogen in the aromatic ring, which may be in any position. $R^1$ is any substituent for quinolinyl described herein.

The starting material for the aldehydes, formula 1, can be obtained via methods such as those found in the references listed below. Those skilled in the art using an appropriate synthetic approach and method can produce the aldehydes depicted in formula 1. Appropriate methods include use of reductions such as Wolff-Kishner type in conjunction with hydride reduction/elimination methods and subsequent oxidations such as the Swern/Moffat type or use of the Dess-martin periodinane. Use of van Leusen's reagent, methylated-TosMIC (see: van Leusen, A. M.; at al. *Tetrahedron Lett.* 3487, 1975. and *Alpha-tosylbenzyl isocyanide*; Organic Syntheses, Hart, D. J. Ed. by Sisko, J. et al. 198 (77) 1999 and Horne et al *Heterocycles*, 139, 39, 1994.) gives the desired methyl imidazole compounds such as those of formula 2.

For the starting material for general synthetic methods in Scheme I see procedures and references found in the following items.

Preparation of 4-(2-methyl-5,6,7,8-tetrahydro-quinolin-7-yl-methyl)-1,3-dihydro-imidazole-2-thione as specific alpha2B adrenergic receptor agonist, and methods of using the same. Heidelbaugh, Todd M.; Chow, Ken; Nguyen, Phong; Gil, Daniel; Donello, John E. US 2005075366 A1

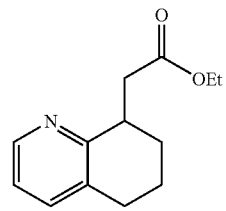

ethyl 2-(5,6,7,8-tetrahydroquinolin-8-yl)acetate

Bicyclic alpha-amino acids. IV: Synthesis of 3-(1-tetralinyl)- and 3-(5,6,7,8-tetrahydro-5-quinolinyl)alanine. Reimann, Eberhard; Dammertz, Archiv der Pharmazie (1983), 316 (4), 297-302.

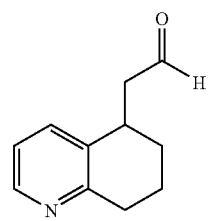

2-(5,6,7,8-tetrahydroquinolin-5-yl)acetaldehyde

A new method for introducing a carbalkoxymethyl group into pyridocycloalkanones. Wu, Edwin S. C.; Kover, Alexander. *Synthetic Communications* (1994), 24(2), 273-8.

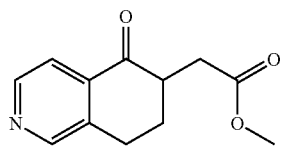

methyl 2-(5-oxo-5,6,7,8-tetrahydroisoquinolin-6-yl)acetate

Preparation of novel fused pyridazine compounds as anti-allergic and anti-inflammatory agents. Bantick, John; Hirst, Simon; Perry, Matthew. (1997) WO 9745428 A1

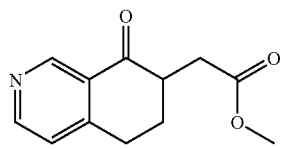

methyl 2-(8-oxo-5,6,7,8-tetrahydroisoquinolin-7-yl)acetate

7-Isoquinolineacetic acid derivatives. Chorvat, Robert J.; Pappo, Raphael. (1976), U.S. Pat. No. 3,991,061 Application: US 75-596509

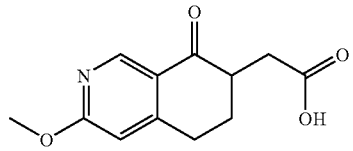

2-(3-methoxy-8-oxo-5,6,7,8-tetrahydroisoquinolin-7-yl) acetic acid

Preparation of fused pyridines as antidiabetics. Ge, Min; Yang, Lihu; Zhou, Changyou; Lin, Songnian; Cline, Eric Dean. WO 2006083612 A1

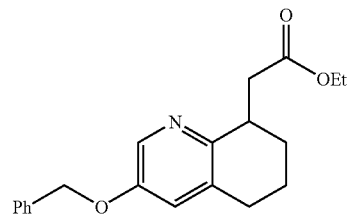

ethyl 2-(3-(benzyloxy)-5,6,7,8-tetrahydroquinolin-8-yl)acetate

Synthesis of enantiomerically pure 8-substituted 5,6,7,8-tetrahydroquinolines. Uenishi, Junichi; Hamada, Masahiro. *Synthesis* (2002), (5), 625-630.

Preparation of novel fused pyridazine compounds as anti-allergic and anti-inflammatory agents. Bantick, John; Hirst, Simon; Perry, Matthew. WO 9745428 A1

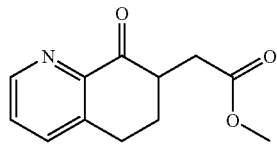

methyl 2-(8-oxo-5,6,7,8-tetrahydroquinolin-7-yl)acetate

Synthesis of functionalized quinoline derivatives by annulation of pyridines. Ghera, Eugene; Ben David, Yoshua; Rapoport, Henry. *Journal of Organic Chemistry* (1981) 46(10), 2059-65.

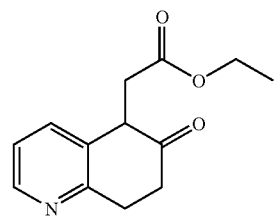

ethyl 2-(6-oxo-5,6,7,8-tetrahydroquinolin-5-yl)acetate 7,8-dihydro-5(6H)quinolones. Potential intermediates for the synthesis of Pumiliotoxin C. Bennett, Gregory B.; Minor, Harold. *Journal of Heterocyclic Chemistry* (1979), 16(4), 633-5.

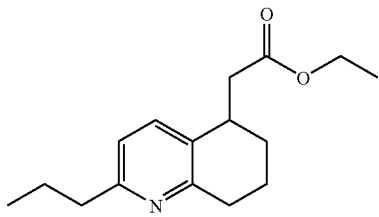

ethyl 2-(2-propyl-5,6,7,8-tetrahydroquinolin-5-yl)acetate

Scheme II

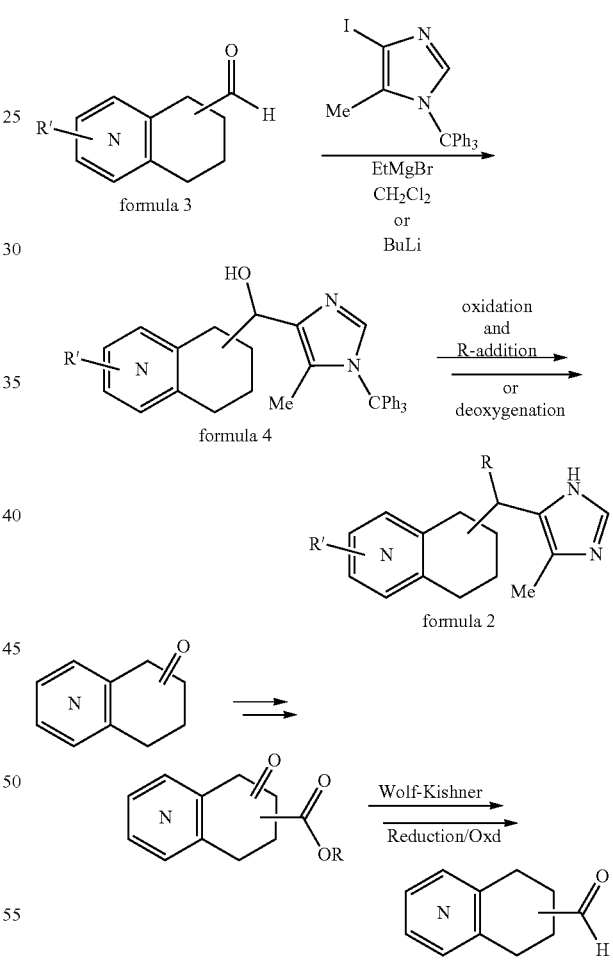

The aldehydes of formula 3 can be obtained via methods such as those found in the references listed below or by the general route outlined above. Addition of 4-iodo-5-methyl-1-trityl-1H-imidazole is accomplished through metallation-addition chemistry by use of ethylmagnesium bromide or a butyllithium such as nBuLi, sBuLi or tBuLi. 4-Iodo-5-methyl-1-trityl-1H-imidazole metallation may require protection of the 2-position (eg. the TBS group). The alcohol of formula 4 is converted to the desired compound of formula 2 by appropriate oxidation and R-addition (such as alkyl Grignards) or a deoxygenation protocol such as hydrogenolysis, elimination/reduction protocol (MsCl/NEt₃, followed by treatment with TFA and hydrogenation: H₂ mediated by Pt or Pd catalysis) or other direct deoxygenation methods known to those skilled in the art.

For the aldehydes of formula 3 see procedures and references found in the following items.

Preparation of A-form crystals of tetrahydroquinoline derivative and their medical compositions and pharmaceuticals. Sugimoto, Yuichi; Miyazoe, Hiroshi; Tsujita, Tomohiro. JP 2006241096 A2

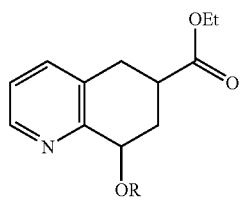

ethyl 8-methoxy-5,6,7,8-tetrahydroquinoline-6-carboxylate

A formal synthesis of (+)-Huperzine A. Haudrechy, Arnaud; Chassaing, Christophe; Riche, Claude; Langlois, Yves. *Tetrahedron* 2000, 56 (20), 3181.

Preparation of methyl 2-Methoxycarbonylmethyl-6-Oxo-1,6-Dihydropyridine-3-Carboxylate. Feng, Song; He, Xuchang; Yu, Gengli; Yu, Xia; Bai, Donglu. *Organic Preparations and Procedures International* (2004), 36(2), 129-133.

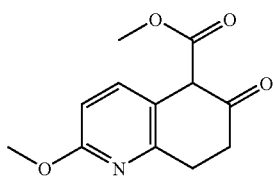

methyl 2-methoxy-6-oxo-5,6,7,8-tetrahydroquinoline-5-carboxylate

Syntheses of polycyclic ring systems based on the new generation of o-quinodimethanes. Ito, Yoshihiko; Nakatsuka, Masashi; Saegusa, Takeo. *Journal of the American Chemical Society* 1982, 104(26), 7609-22.

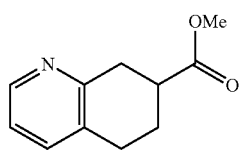

methyl 5,6,7,8-tetrahydroquinoline-7-carboxylate

Nonsteroidal inflammation inhibitor. 3. Substituted azatetralin- and azaindan carboxylic acids with antiinflammatory action. Schroeder, Eberhard; Lehmann, Manfred; Boettcher, Irmgard. *European Journal of Medicinal Chemistry* 1979, 14(4), 309-15.

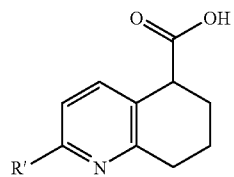

2-methyl-5,6,7,8-tetrahydroquinoline-5-carboxylic acid

Synthesis of 1-azadeazaberbine. Klar, H.; Zymalkowski, F. *Archiv der Pharmazie* 1974, 307(8), 577-84.

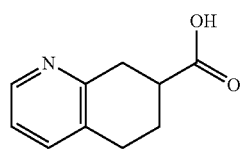

5,6,7,8-tetrahydroquinoline-7-carboxylic acid

Scheme III

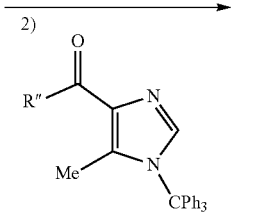
formula 5

1) deprotonation (nBuLi)
2)

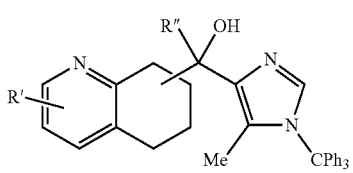
formula 6 deoxygenation
1) MsCl/NEt₃
2) TFA/
H₂ + cat
reduction or
oxidation
and or
R-addition

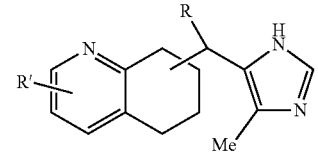
formula 2

The tetrahydroquinolines of formula 5, can be obtained commercially or synthesized by various methods including hydrogenation of a quinoline in the presence of TFA or other suitable solvent system. Deprotonation is accomplished through use of butyl lithium such as nBuLi followed by addition of 1-(5-methyl-1-trityl-1H-imidazol-4-yl)ethanone or 5-methyl-1-trityl-1H-imidazole-4-carbaldehyde. The alcohol of formula 6 is converted to the desired 9 compound of formula 2 by appropriate oxidation and/or R-addition (such as alkyl Grignards) to or a deoxygenation protocol such as elimination/reduction protocol (MsCl/NEt₃, followed by it treatment with TFA and hydrogenation) or other direct deoxygenation methods known to those skilled in the art.

Preparation of (+)-7-(5-Methyl-1H-imidazol-4-ylmethyl)-5,6,7,8-tetrahydro-quinoline (8)

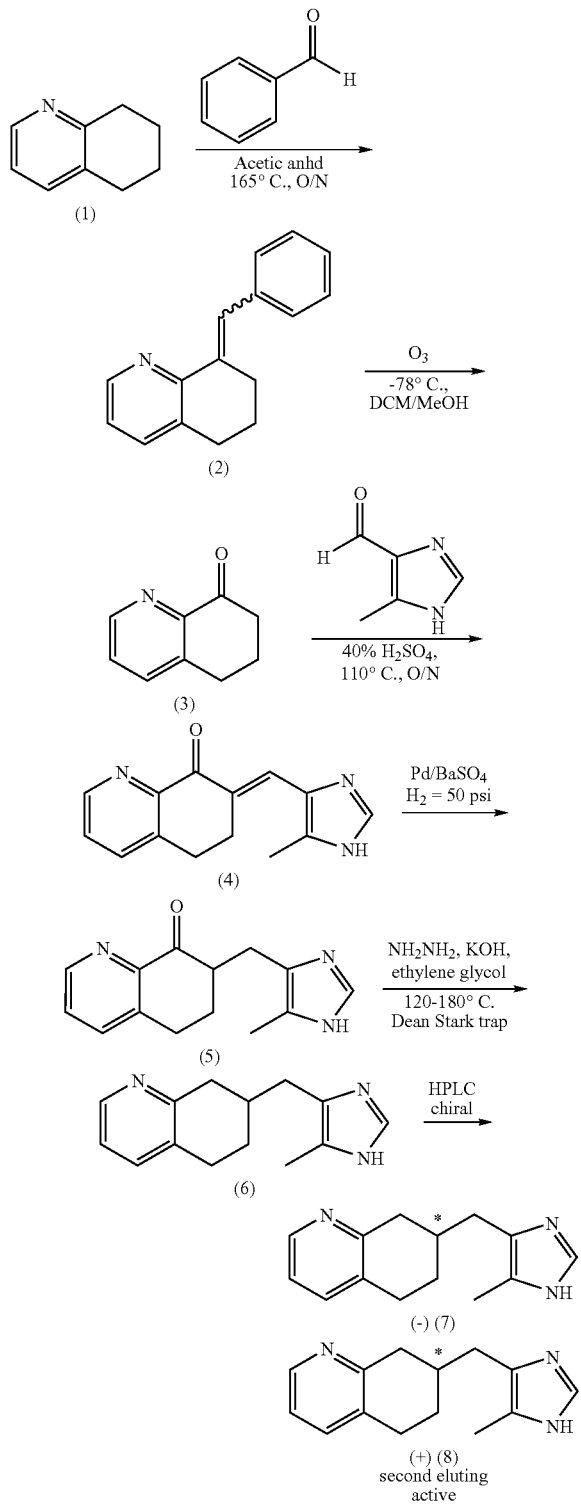

8-Benzylidene-5,6,7,8-tetrahydro-quinoline (2): A solution of 5,6,7,8-tetrahydroquinoline (18.2 g, 137 mmol), benzaldehyde (17.7 g, 166. mmol), and acetic anhydride (24.5 mL, 254 mmol) was heated at 165° C. for 16 h. The reaction mixture was cooled to room temperature (rt). Crushed ice was added, and the mixture was slowly basified with NaOH (solid and 2 M NaOH) to pH ~7. The aqueous layer was extracted with hexane/ethyl acetate (1:1 solution) 3 times. The pooled organic layers were dried over magnesium sulfate. The mixture was filtered, and the solvents were removed under vacuum to give 8-benzylidene-5,6,7,8-tetrahydro-quinoline (2) as a brown solid.

6,7-Dihydro-5H-quinolin-8-one (3): A solution of (2) in dichloromethane (100 mL) and methanol (500 mL) was cooled to −78° C. and charged with ozone/oxygen (3 psi, 1.5 ampere). The dark brown solution turned yellow after several hours. When (2) was consumed (TLC), ozone/oxygen flow was stopped. The reaction mixture was purged with nitrogen for 10 m. Methyl sulfide (6 mL) was added, and the mixture was stirred for 30 m at 0° C. The solvents were removed under vacuum and the residue was dissolved in 1 N HCl (500 mL) and washed with diethyl ether (4×150 mL). The aqueous layer was basified to pH ~7 with NaOH (s), and extracted with ethyl acetate (2×200 mL). The pooled ethyl acetate layers were dried over magnesium sulfate. The mixture was filtered and the solvent was removed under vacuum. The residue was purified by chromatography on silica gel with 90% EtOAc 10% hexane to give 6,7-Dihydro-5H-quinolin-8-one (3) as a solid. The aqueous layer was extracted with chloroform/isopropanol (3:1) several times. The pooled chloroform/isopropanol layers were dried over magnesium sulfate. The mixture was filtered and the solvents were removed under vacuum to give (3). The combined weight of (3) was 17.9 g (122 mmol, 89% over 2 steps).

(E)-7((5-Methyl-1H-imidazol-4-yl)methylene)-6,7-dihydroquinolin-8(5H)-one (4): A solution of (3) (0.990 g, 6.73 mmol) and 5-methyl-1H-imidazole-4-carbaldehyde (0.890 g, 8.05 mmol) in 40% sulfuric acid (10 mL) was heated at 110° C. for 16 h. The reaction was cooled to rt. Crushed ice was added and the mixture was stirred vigorously, while NaOH(s) was added carefully. At pH ~6 the product precipitated from solution. The mixture was stirred for 30 m at room temperature, and filtered to isolate (E)-7-((5-Methyl-1H-imidazol-4-yl)methylene)-6,7-dihydroquinolin-8(5H)-one (4) as a yellow solid, 1.39 gram (5.81 mmol, 86% yield).

7-((5-Methyl-1H-imidazol-4-yl)methyl)-6,7-dihydroquinolin-8(5H)-one (5): A mixture of (4) (1.39 g, 5.81 mmol) and Pd/BaSO₄ (5 wt %, 0.47 g) in methanol and chloroform was hydrogenated at 50 psi for one hour. The reaction mixture was filtered through a bed of Celite, and washed with methanol. The solvents were removed under vacuum. The crude product was purified by chromatography on silica gel with 2 to 3% ammonia saturated methanol in dichloromethane to give 7-((5-Methyl-1H-imidazol-4-yl)methyl)-6,7-dihydroquinolin-8(5H)-one (5) as a yellow oil (0.830 g, 344 mmol, 59% yield).

7-((5-Methyl-1H-imidazol-4-yl)methyl)-5,6,7,8-tetrahydroquinoline (6): A mixture of (5) (0.83 g, 344 mmol), potassium hydroxide (0.782 g, 13.9 mmol), and hydrazine hydrate (0.77 mL, 24.7 mmol) in ethylene glycol (20 mL) was heated at 120° C. in an apparatus fitted with a Dean Stark trap for 1 h, and at 180° C. for 4 hours. The reaction was cooled to rt, and diluted with water. The aqueous medium was extracted three times with chloroform/isopropanol (3:1, 200 mL). The pooled organic layers were dried over magnesium sulfate. The mixture was filtered and the solvents were removed under vacuum. The residue was purified by chromatography on silica gel with 2 to 3% ammonia saturated methanol in dichloromethane to give 7-(5-methyl-1H-imidazol-4-ylmethyl)-5,6,7,8-tetrahydro-quinoline (6) as a foam (0.544 g, 2.40 mmol, 70% yield). $^1$H NMR (300 MHz, CDCl$_3$): δ 8.30 (d, J=3.90 Hz, 1H), 7.43 (s, 1H), 7.37 (d, J=7.50 Hz, 1H), 7.03 (dd, J=7.50, 4.80 Hz, 1H), 2.99-2.91 (m, 1H), 2.84-2.76 (m, 2H), 2.70-2.50 (m, 3H), 2.24-2.14 (m, 1H), 2.15 (s, 3H), 2.04-1.96 (m, 1H), 1.54-1.40 (m, 1H).

Compound (6) was separated by chiral HPLC: CHIRALCEL® OD with 85% hexane and 15% ethanol at rt. The (+)-7-(5-methyl-1H-imidazol-4-ylmethyl)-5,6,7,8-tetrahydro-quinoline (8) corresponding to the second eluting peak was active in an in vitro assay. The (−)-7-(5-methyl-1H-imidazol-4-ylmethyl)-5,6,7,8-tetrahydro-quinoline (7) was the first eluting peak, and was inactive.

Other alternate routes to a wide variety of compounds are readily apparent to those skilled in the art.

These compounds will be useful for the treatment of mammals, including humans, with a range of conditions and diseases that include, but are not limited to, ischemic neuropathies, optic neuropathy, neuropathic pain, visceral pain, corneal pain, headache pain, migraine, cancer pain, back pain, irritable bowel syndrome pain, muscle pain and pain associated with diabetic neuropathy, the treatment of diabetic retinopathy, other retinal degenerative conditions, cognitive deficits, neuropsychiatric conditions, drug dependence and addiction, withdrawal symptoms, spasticity, autism, Huntington's disease, attention deficit disorder, attention deficit hyperactivity disorder ADHD, obsessive-compulsive disorders, Tourette's disorder, Parkinson's ALS, and other motor or movement disorders and diseases.

Other uses include dilation of the pupil, increase blood pressure, treating nasal congestion, and vasoconstriction in ocular tissue.

These compounds may be formulated into solid, liquid, or other types of dosage forms using methods known in the art. Both formulation of dosage forms and determination of a therapeutically effective dose can be readily made by a person of ordinary skill using routine methods.

EC50

(IA)

The foregoing description details specific methods and compositions that can be to employed to practice the present invention, and represents the best mode contemplated. However, it is apparent for one of ordinary skill in the art that further compounds with the desired pharmacological properties can be prepared in an analogous manner, and that the disclosed compounds can also be obtained from different starting compounds via different chemical reactions. Similarly, different pharmaceutical compositions may be prepared and used with substantially the same result. Thus, however detailed the foregoing may appear in text, it should not be construed as limiting the overall scope hereof; rather, the ambit of the present invention is to be governed only by the lawful construction of the claims.

What is claimed is:

1. A compound of the formula

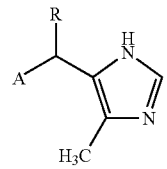

wherein R is H, C$_{1-4}$ alkyl, or CF$_3$;

A is tetrahydroquinolinyl having 0, 1, 2, or 3 stable substituents consisting of from 1 to 8 heavy atoms and any required hydrogen atoms, said heavy atoms being selected from C, N, O, S, F, Cl, Br, I, and any combination thereof.

2. The compound of claim 1 wherein R is H.

3. The compound of claim 1 wherein said substituents are selected from CH$_3$, ethyl, t-butyl, ethenyl, ethynyl, OCH$_3$, NHMe, NMe$_2$, Br, Cl, F, phenyl, and combinations thereof.

4. The compound of claim 1 wherein A is unsubstituted.

5. The compound of claim 1 having the formula

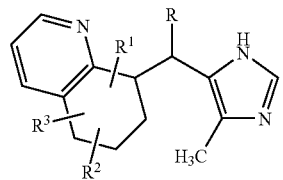

wherein R$^1$, R$^2$, and R$^3$ are independently hydrogen or stable substituents consisting of from 1 to 8 heavy atoms and any required hydrogen atoms, said heavy atoms being selected from C, N, O, S, F, Cl, Br, I, and any combination thereof; and n is 0, 1, 2, or 3.

6. The compound of claim 5 having the formula

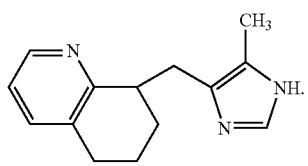

7. The compound of claim 1 having the formula

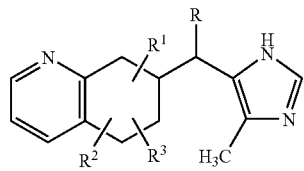

wherein R$^1$, R$^2$, and R$^3$ are independently hydrogen or stable substituents consisting of from 1 to 8 heavy atoms and any required hydrogen atoms, said heavy atoms being selected from C, N, O, S, F, Cl, Br, I, and any combination thereof; and n is 0, 1, 2, or 3.

8. The compound of claim 7 having the formula

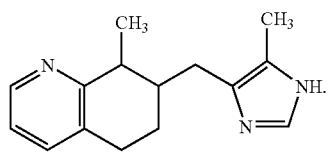

9. The compound of claim 2 selected from:
(+)-7-(5-Methyl-1H-imidazol-4-ylmethyl)-5,6,7,8-tetrahydro-quinoline, and
(−)-7-(5-Methyl-1H-imidazol-4-ylmethyl)-5,6,7,8-tetrahydro-quinoline.

10. The compound according to claim 1 wherein R is methyl.

11. The compound according to claim 1 wherein R is ethyl.

12. The compound according to claim 1 wherein R is $CF_3$.

13. A method comprising administering a compound according to claim 1 to a patient in need thereof for the treatment of glaucoma or ocular hypertension.

14. A method comprising administering a compound according to claim 1 to a patient in need thereof for the treatment of pain.

15. A method comprising administering a compound according to claim 1 to a patient in need thereof for the treatment of nasal congestion.

* * * * *